United States Patent [19]

Dostert et al.

[11] 4,434,170
[45] Feb. 28, 1984

[54] NOR-TROPANE DERIVATIVES, AND THEIR APPLICATION IN THERAPEUTICS

[75] Inventors: Philippe Dostert, Paris; Thierry Imbert, Noisy; Bernard Bucher, Marnes la Coquette, all of France

[73] Assignee: Delalande S.A., Courbevoie, France

[21] Appl. No.: 318,244

[22] Filed: Nov. 4, 1981

[30] Foreign Application Priority Data

Nov. 7, 1980 [FR] France ............................... 80 23785

[51] Int. Cl.³ .................... A61K 31/46; C07D 451/04
[52] U.S. Cl. .................................. 424/265; 546/112; 546/124; 546/125
[58] Field of Search ................... 546/112, 124, 125; 424/265

[56] References Cited

U.S. PATENT DOCUMENTS

| | | | |
|---|---|---|---|
| 3,134,782 | 5/1964 | Archer et al. | 546/124 |
| 4,179,567 | 12/1979 | Clarke et al. | 546/124 |
| 4,273,778 | 6/1981 | Hadley et al. | 424/265 |

FOREIGN PATENT DOCUMENTS

| | | | |
|---|---|---|---|
| 374679 | 3/1964 | Switzerland | 546/129 |
| 774858 | 5/1957 | United Kingdom | 546/125 |

Primary Examiner—Alan L. Rotman
Attorney, Agent, or Firm—Flynn, Thiel, Boutell & Tanis

[57] ABSTRACT

Novel 3 β-aroylamino and 3 β-heteroaroylamino nor-tropanes and granatanes are provided having the general formula:

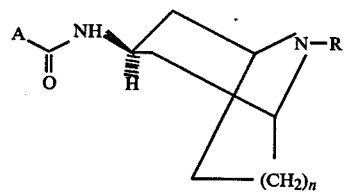

Wherein n=1 or 2, R represents a benzyl or a substituted benzyl group and A–CO represents one of a specific range of aroyl groups. The compounds of the invention are useful in the treatment of psychism or digestive troubles.

16 Claims, No Drawings

NOR-TROPANE DERIVATIVES, AND THEIR APPLICATION IN THERAPEUTICS

The present invention relates to new nor-tropane and granatane derivatives, more especially to new 3-aroylamino and 3-heteroaroylamino nor-tropanes and granatanes, respectively substituted in position -8 and -9, the process for preparing same and the application of same in therapeutics.

These new compounds correspond more precisely to the general formula:

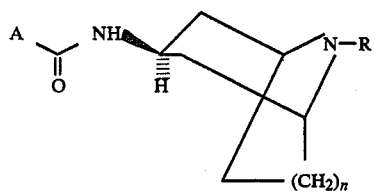

(I)

in which:

n assumes the values 1 or 2;

R represents a benzyl group; a benzyl group substituted by one or two halogen atoms, a methyl group or a cyano group or a (furyl-3)methyl chain; and —A—CO represents:

a pyrimidinic group of structure:

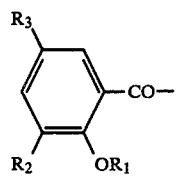

in which $R_1$ represents a methyl or ethyl group; $R_2$ represents an alkyloxy group with 1 or 2 carbon atoms or an amino group; and $R_3$ represents a hydrogen atom, a bromine atom or a methoxy group, a nitro group, an acetyl group or an alkylmerçapto group with 1 or 2 carbon atoms; the whole ($R_3$, n, R) however not being able to assume the value (H, 1, benzyl); or an aromatic group of structure:

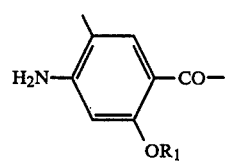

in which $R_1$=$CH_3$ or $C_2H_5$ and x=Br or Cl, the whole (X, n, $R_1$, R) however not being able to assume the following values:

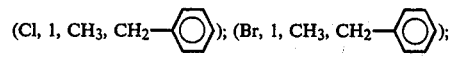

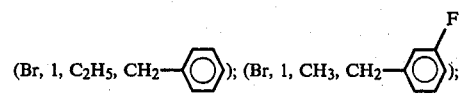

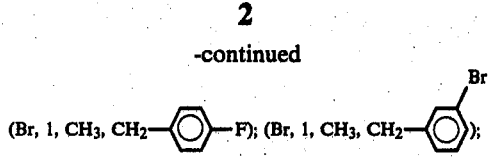

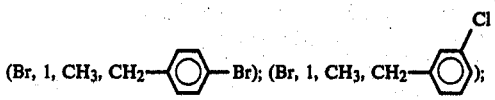

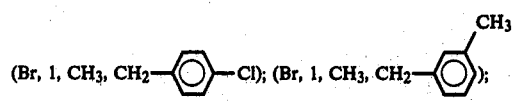

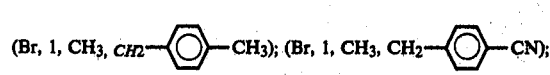

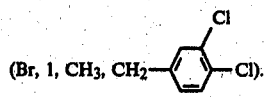

The compounds preferred among those of formula (I) are the compounds for which the pair (n, R) assumes the value:

(1, benzyl) and the whole ($R_1$, $R_2$, $R_3$) assumes the following values: ($CH_3$, $NH_2$, Br); ($C_2H_5$, $OC_2H_5$, H), ($CH_3$, $OCH_3$, $OCH_3$); ($C_2H_5$, $OCH_3$, H); ($CH_3$, $OC_2H_5$, H); ($C_2H_5$, $OCH_3$, $OCH_3$); ($CH_3$, $OCH_3$,$NO_2$); ($CH_3$, $OCH_3$, Br); ($CH_3$, $OCH_3$, $SCH_3$); ($CH_3$, $OCH_3$, $C_2H_5S$); ($CH_3$, $OCH_3$, $COCH_3$);

(2, benzyl) and the whole ($R_1$, $R_2$, $R_3$) assumes the values ($C_2H_5$, $OCH_3$, H), ($CH_3$, $OCH_3$, H);

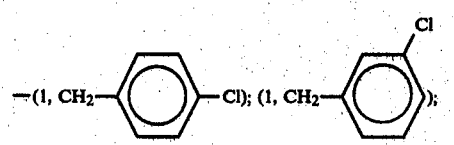

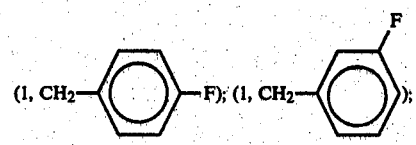

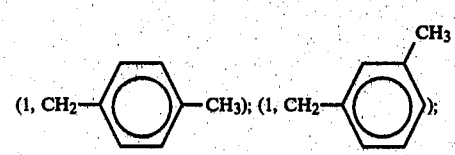

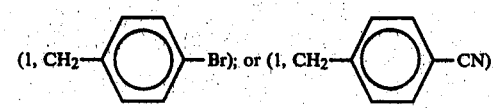

and the whole ($R_1$, $R_2$, $R_3$) assumes the value ($CH_3$,$OCH_3$, H);

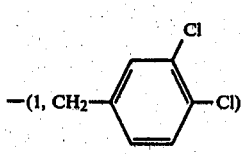

and the whole ($R_1$, $R_2$, $R_3$) assumes the value ($C_2H_5$,$OCH_3$, H);

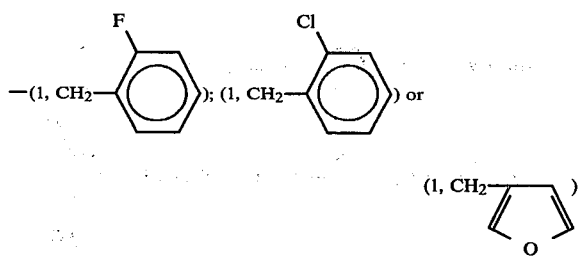

and the pair $(R_1, X) = (CH_3, Br)$;

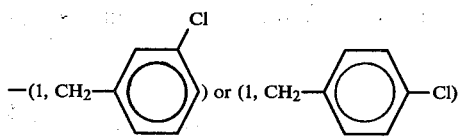

and the pair $(R_1, X)$ assumes the value $(C_2H_5, Br)$, or

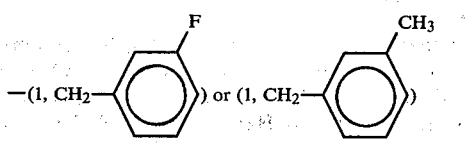

and the pair $(R_1, X)$ assumes the value $(CH_3, Cl)$.

It should be noted that in formula (I) the A—CO—NH chain is in the equatorial position and the tropanes, nor-tropanes and granatanes having such a substituent in the equatorial position will be called β in what follows.

The present invention of course also relates to the salts of the compounds of formula (I) and more precisely the pharmaceutically mineral or organic acid addition salts.

The compounds of formula (I) of the invention are obtained by condensing, by means of the mixed anhydride method, the acids of formula:

A—COOH                    (II)

in which A—CO has the same meaning as in formula (I), with the 3 β-amino nor-tropanes and 3 β-amino granatanes of formula:

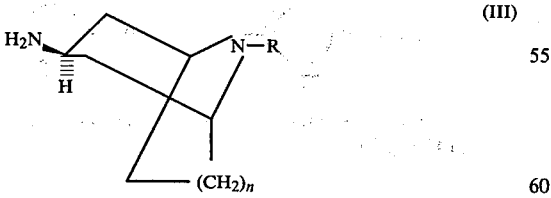

(III)

in which R and n have the same meanings as in formula (I).

The compounds of formula (I) of the invention, except those for which $R_2$ represents an amino group and those for which the A—CO pattern has the following structure:

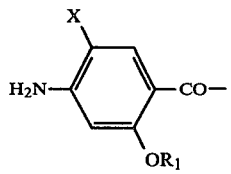

where $R_1$ and X have the same meanings as above, may also be obtained by condensing, preferably in a tetrahydrofuranic medium and in the presence of triethylamine, the compounds of formula (III) previously defined, with the acid chlorides of the compounds of formula:

A'—COOH                    (II')

where A'—CO has the same meaning as A—CO in formula (I) with however the above stated restrictions as regards $R_2$ and without being able to have the structure:

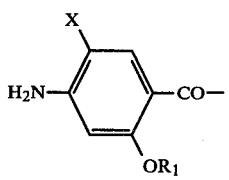

Finally, the compounds of formula (I) of the invention, except those for which the A—CO pattern has the particular structure:

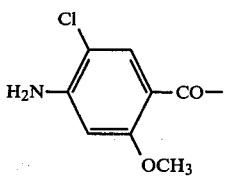

and those for which R represents a benzyl group, may also be prepared by condensation of the compounds of formula:

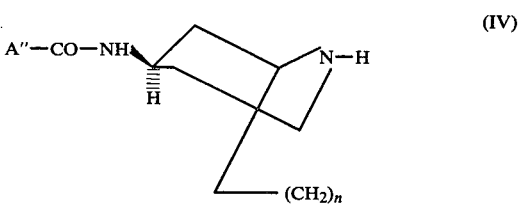

(IV)

in which n=1 or 2 and A''—CO has the same meanings as A—CO in formula (I) with however the above stated restrictions, with the compounds of formula:

X'—R'                    (V)

where X' is a chlorine or bromine atom or a mesyloxy or tosyloxy group, and R' has the same meaning as R in formula (I) without however being able to represent a benzyl group, this condensation reaction being carried out preferably at reflux in an organic solvent such as acetone, acetonitrile or DMF and in the presence of a base such as potassium carbonate or triethylamine.

The compounds of formula (III) may be prepared in accordance with the processes described in French patent application No. 2 446 823 and Belgian Pat. No. 881 134.

The compounds of formula (IV) are obtained by hydrogenolysis, preferably in an acid alcohol medium, at ambient temperature, at a pressure of 90 m bars and in the presence of palladium on carbon (10% of palladium) of the compounds of formula (I) having the particular structure:

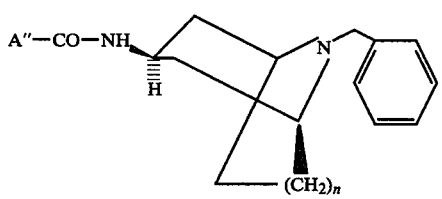
(Ia)

in which n and A″—CO have the same meanings as in formula (IV), A″—CO not however being able to represent the pattern:

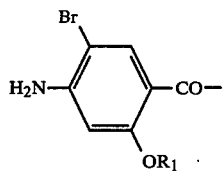

where $R_1$ has the same meanings as in formula (I), and the compounds of formula (IV) having the particular structure:

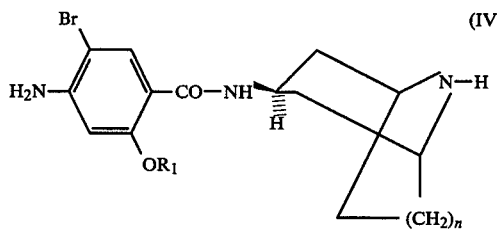
(IVa)

in which $R_1$ and n have the same meanings as in formula (I), are obtained by bromation, preferably in an acetic acid medium, of the compounds of formula:

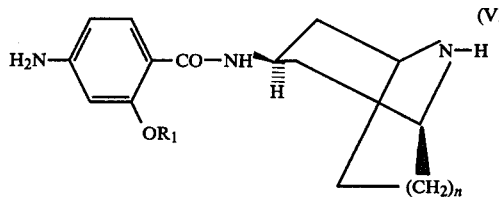
(VI)

in which $R_1$ and n have the same meanings as in formula (IVa).

The compounds of formula (VI) are themselves obtained by hydrogenolysis of the compounds of formula (I) having the particular structure:

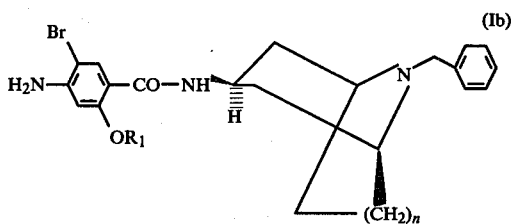
(Ib)

in which $R_1$ and n have the same meanings as in formula (IV).

Some compounds of formula (II) are new. It is a question more precisely of those having the particular formula:

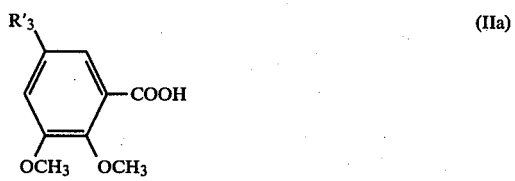
(IIa)

in which $R_3'$ represents an alkylmercapto group with 1 or 2 carbon atoms or an acetyl group.

The compounds of formula (IIa) for which $R_3'$ represents an alkylmercapto group with 1 or 2 carbon atoms are obtained by a two step process which consists in reducing by means of tin in a hydrochoric medium, the compound of formula:

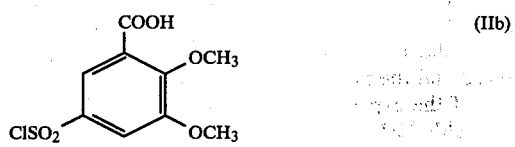
(IIb)

then in treating the intermediate compound thus obtained with the corresponding alkyl sulfate having 1 to 2 carbon atoms in the presence of aqueous sodium hydroxide.

The compound of formula (IIb) is obtained by treating, by means of chlorosulfonic acid ($ClSO_3H$), the compound of formula:

(IIc)

The compound of formula (IIa) for which $R_3'$ represents an acetyl group is obtained by oxidizing, by means of the pyridinium chloride-chromic oxide complex, the compound of formula:

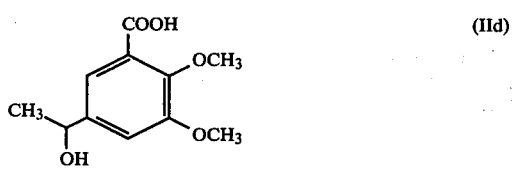
(IId)

Finally, the compound of formula (IId) is obtained by a two stage process which consists in treating the compound of formula:

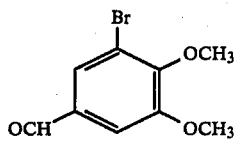 (IIe)

by means of a lithium containing derivative of formula $CH_3$-Li, then in reacting, on the intermediate compound thus obtained, carbon dioxide.

The following preparations are given by way of example to illustrate the invention.

EXAMPLE 1:

3β-[(2,3-diethoxy) benzoyl]amino 8-benzyl nor-tropane hydrochloride (I)

Code number: 115

A solution of 10 g of 2,3-diethoxybenzoic acid in 30 ml of thionyl chloride is brought to reflux for 3 hours, then the thionyl chloride is evaporated, the residue is taken up in toluene, the toluene is evaporated and the residue is slowly added to a solution cooled to 0° C. of 10 ml of triethylamine and 9.85 g of 3β-amino 8-benzyl nor-tropane in 250 ml of tetrahydrofuran. It is left to return to ambient temperature with stirring for 2 h 30 mn, filtered, the filtrate is evaporated, the residue is taken up in carbonated water, extracted with methylene chloride, washed with water, dried on sodium sulfate, filtered and the filtrate evaporated. The residue is dissolved in 150 ml of ethyl acetate and 9.17 ml of 4N ethanolic hydrochloric acid are added. Then it is filtered and the precipitate recrystallized in ethanol. Thus 6 g of the expected compound were obtained.

Yield: 82%
Melting point: 220° C.
Empirical formula: $C_{25}H_{33}ClN_2O_3$
Molecular weight: 444.987
Elementary analysis

|  | C | H | N |
|---|---|---|---|
| Calculated (%) | 67.47 | 7.48 | 6.31 |
| Obtained (%) | 67.28 | 7.42 | 6.51 |

By the same process, but from the corresponding reagents, the compounds of formula (I) were obtained having code numbers: 112, 113, 118, 120, 129, 135, 139 to 143, 145, 147, 148, 155, 168, 171, 173 and 174 and appearing in table I below.

EXAMPLE 2:

3β-(2,3-dimethoxy benzoyl) amino 8-parachloro benzyl nor-tropane (I)

Code number: 112

To a solution, cooled to 0° C., of 17 g of (2,3-dimethoxy)benzoic acid and 10.1 ml of triethylamine in 350 ml of methylene chloride, are added 6.85 ml of ethyl chloroformiate. After 30 mn at 0° C., 15.6 g of 3β-amino 8-parachloro benzyl nor-tropane are slowly added. It is agitated for an hour at ambient temperature, then washed with water, decanted, the organic phase is evaporated and the residue crystallized in an isopropylic ether/ethyl acetate (75/25) mixture. After recrystallization in acetone the expected compound is obtained:

Yield: 75%
Melting point: 131° C.
Empirical formula: $C_{23}H_{27}Cl\,N_2O_3$
Molecular weight: 414.919
Elementary analysis:

|  | C | H | N |
|---|---|---|---|
| Calculated (%) | 66.57 | 6.56 | 6.75 |
| Obtained (%) | 66.67 | 6.70 | 6.75 |

By the same process, but from the corresponding reagents, the compounds of formula (I) are obtained having code numbers 106, 113, 115, 118, 120, 121, 123, 126, 127, 129, 131, 132, 135, 139 to 143, 145, 147, 148, 155, 168, 169, 171, 173, 174 and 180 appearing in table I below.

EXAMPLES 3:

3β-[(2,3-dimethoxy) benzoyl] amino 8-metafluorobenzyl nor-tropane (I)

Code number: 113

A suspension of 8 g of 3β-[(2,3-dimethoxy) benzoyl] amino nor-tropane [(IV), code number 111, prepared in example 4], 5.18 g of metafluorobenzyl chloride and 11.4 of potassium carbonate in 100 ml of acetone is brought to reflux for 12 hours. Then it is filtered, the filtrate evaporated, the residue taken up in methylene chloride washed with water, dried on sodium sulfate, filtered, the filtrate is evaporated and the residue crystallized in petroleum ether. After recrystallization in isopropylic ether, 8.6 g of the expected product are obtained.

Yield: 78%
Melting point: 97° C.
Empirical formula: $C_{23}H_{27}FN_2O_3$
Molecular weight: 398.462
Elementary analysis:

|  | C | H | N |
|---|---|---|---|
| Calculated (%) | 69.32 | 6.83 | 7.03 |
| Obtained (%) | 69.34 | 6.75 | 6.94 |

By the same process, but from the corresponding reagents, the compounds of formula (I) are obtained appearing in table I below under the code numbers: 112, 118, 120, 121, 123, 126, 129, 131, 132, 145, 155, 169, 173 and 180.

EXAMPLE 4:

3β-[(2,3-dimethoxy)benzoyl] amino nor-tropane (IV)

Code number: 111

A suspension of 87.9 g of 3β-[(2,3-dimethoxy)benzoyl] amino 8-benzyl nor-tropane (I) and 18 g of 10% palladium carbon (in a 50% suspension in water) in 900 ml of ethanol at 96°, is hydrogenolyzed in an autoclave at a pressure of 90 m bars. Then it is filtered, the filtrate evaporated, the residue is taken up in water, alkalized with sodium carbonate, extracted with methylene chloride, dried on sodium sulfate, and filtered, the filtrate is evaporated, the residue is crystallized in pretroleum ether and recrystallized in ethyl acetate. Thus, 62 g of the expected compound are isolated.

Yield: 92%
Melting point: 119° C.
Empirical formula: $C_{16}H_{22}N_2O_3$
Molecular weight: 290.352
Elementary analysis:

|  | C | H | N |
|---|---|---|---|
| Calculated (%) | 66.18 | 7.64 | 9.65 |
| Obtained (%) | 66.23 | 7.38 | 9.87 |

By the same process, but from the corresponding reagents, the compounds of formula (IV) were obtained, required for the synthesis of the compounds of formula (I) according to example 3, as well as the compounds of formula (VI), more especially 3β-[(4-amino 2-ethoxy) benzoyl] amino nor-tropane [code number: 176; melting point: 200° C.] required for synthesis of the compounds of formula (IVa) according to the following example 5.

EXAMPLE 5:

3β-[(5-bromo 4-amino 2-ethoxy) benzoyl] amino nor-tropane (IVa)

Code number: 177

To a solution of 10 g of 3β-[(4-amino 2-ethoxy) benzoyl] amino nor-tropane in 100 ml of acetic acid, cooled to 10° C., 2 ml of bromine are slowly added. This it is left to return to ambient temperature, the precipitate formed is filtered, taken up in isopropylic ether, filtered and recrystallized in 96° alcohol. Thus, 7.4 g of the expected product are obtained.
Yield: 50%
Melting point: >260° C.
NMR spectrum (DMSO): δ(ppm)
=9.3, s, 1 amidic proton: 7.8 and 6.6 s, 2 aromatic protons and 1 amidic proton; 6.00, s, 2 amino protons; 4.00., m, 5 protons: —O—CH$_2$ and 3 tropanic protons (in α of the nitrogen atoms);
2.00, m, 8 tropanic protons;
1.4, t, O—CH$_2$—CH$_3$ (3 protons)

By the same process, but from the corresponding reagents, the compounds of formula (IVa) are obtained, required for the synthesis of the corresponding compounds of formula (I) in example 3.

EXAMPLE 6:

5-methylmercapto 2,3-dimethoxy benzoic acid [(IIa), $R_3' = SCH_3$]

To a solution, cooled to −5° C., of 511.7 g (200 ml) of chlorosulfonic acid (ClSO$_3$H) are slowly added 80 g of 2,3-dimethoxy benzoic acid. Then the temperature is allowed to rise to 15° C., the mixture is poured into a solution of water and ice, and the precipitate formed is filtered. Thus, 100 g (yield: 80%) of 5-chlorosulfonyl 2,3-dimethoxy benzoic acid are obtained [(IIb), Melting point: 157° C.].

71 g of this compound are placed in solution in 1 liter of concentrated hydrochloric acid and 30 g of tin are slowly added. Then it is left at ambient temperature for a night, the precipitate formed is filtered, recrystallized in isopropylic ether and dissolved in an aqueous solution of 40 g of sodium hydroxide in 800 ml of water. Then 63 g of methyl sulfate are slowly added and it is left for a night of ambient temperature. Then it is acidified by means of concentrated hydrochloric acid, the precipitate formed is filtered and dried under vacuum. Thus, 34 g of the expected product are isolated.
Yield: 60%
Melting point: 92° C.

By the same process, but from the corresponding reagents, 5-ethylmercapto 2,3-dimethoxy benzoic acid was obtained [(IIa), $R_3' = $S-Et,
Melting point: 66° C.].

EXAMPLE 7:

5-(1-hydroxy ethyl)2,3-dimethoxy benzoid acid [(IId)].

To 310 ml of a 1.4 M methyllithium ethereal solution (cooled to −30° C.) a solution of 30 g of 3-bromo 4,5-dimethoxy benzaldehyde is slowly added while maintaining the temperature at −30° C. Then, after 3 hours of reaction, CO$_2$ gas is added, and the temperature is allowed to rise to 20° C., the mixture is thrown into water, basified with concentrated sodium hydroxide, the ethereal phase is decanted, the aqueous phase is washed with ethyl acetate, then acidified with concentrated hydrochloric acid and extracted with ether. It is dried on sodium sulfate, filtered, the filtrate is evaporated and the residue crystallized in isopropylic ether. 5.9 g of the expected product are obtained.
Yield: 21%
Melting point: 134° C.

EXAMPLE 8:

5-acetyl 2,3-dimethoxy benzoic acid [(IIa), $R_3' = COCH_3$]

A suspension of 8.8 g of compound (IId) obtained in the preceding example and 36 g of manganese dioxide in 100 ml of dioxane is brought to reflux for three hours. Then it is filtered, the filtrate is evaporated and the residue is crystallized in isopropylic ether. 7.2 g of the expected acid are obtained.
Yield: 82%
Melting point: 125° C.
Empirical formula: $C_{11}H_{12}O_5$
Molecular weight: 224.21 p Elementary analysis:

|  | C | H |
|---|---|---|
| Calculated (%) | 58.92 | 5.40 |
| Obtained (%) | 58.43 | 5.41 |

TABLE I
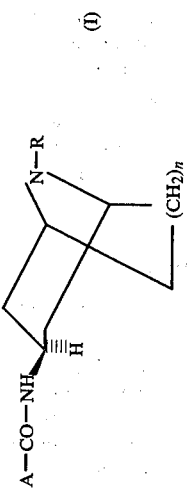
(I)
| Code n° | A—CO— | n | R | Form | Empirical formula | Molecular weight | Melting point (°C.) | Yield (%) | | ELEMENTARY ANALYSIS % | C | H | N |
|---|---|---|---|---|---|---|---|---|---|---|---|---|---|
| 106 | Br-C₆H₂(NH₂)(OMe)-CO— | 1 | C₆H₅-CH₂- | Base | $C_{22}H_{26}BrN_3O_2$ | 444.361 | 122 | 47 | Cal. Obt. | | 59.46 59.25 | 5.90 5.91 | 9.46 9.46 |
| 112 | MeO-C₆H₃(OMe)-CO— | 1 | 4-Cl-C₆H₄-CH₂- | Base | $C_{23}H_{27}ClN_2O_3$ | 414.919 | 131 | 75 | Cal. Obt. | | 66.57 66.67 | 6.56 6.70 | 6.75 6.75 |
| 113 | MeO-C₆H₃(OMe)-CO— | 1 | 3-F-C₆H₄-CH₂- | Base | $C_{23}H_{27}FN_2O_3$ | 398.462 | 97 | 78 | Cal. Obt. | | 69.32 69.34 | 6.83 6.75 | 7.03 6.94 |
| 115 | EtO-C₆H₃(OEt)-CO— | 1 | C₆H₅-CH₂- | HCl | $C_{25}H_{33}ClN_2O_3$ | 444.987 | 220 | 82 | Cal. Obt. | | 67.47 67.28 | 7.48 7.42 | 6.31 6.51 |
| 118 | MeO-C₆H₃(OMe)-CO— | 1 | 3-CH₃-C₆H₄-CH₂- | Base | $C_{24}H_{30}N_2O_3$ | 394.496 | 81 | 60 | Cal. Obt. | | 73.07 72.98 | 7.67 7.69 | 7.10 7.04 |

TABLE I-continued (I)

[Structure: A—CO—NH—[bicyclic core with N—R]—(CH₂)ₙ]

| Code n° | A—CO— | n | R | Form | Empirical formula | Molecular weight | Melting point (°C.) | Yield (%) | | ELEMENTARY ANALYSIS | | |
|---|---|---|---|---|---|---|---|---|---|---|---|---|
| | | | | | | | | | % | C | H | N |
| 120 | [2,3-dimethoxybenzoyl] | 1 | [4-methylcyclohexyl] | Base | C₂₄H₃₀N₂O₃ 1/6 H₂O | 397.499 | 99 | 74 | Cal. Obt. | 72.51 72.55 | 7.69 7.85 | 7.05 6.99 |
| 121 | [5-bromo-4-amino-2-methoxybenzoyl] | 1 | [2-chlorobenzyl] | Base | C₂₂H₂₅BrClN₃O₂ | 478.810 | 215 | 75 | Cal. Obt. | 55.18 55.13 | 5.26 5.41 | 8.78 8.63 |
| 123 | [4-bromo-5-amino-2-ethoxycyclohexanoyl] | 1 | [4-chlorobenzyl] | Base | C₂₃H₂₇BrClN₃O₂ | 492.836 | 150 | 84 | Cal. Obt. | 56.05 55.92 | 5.52 5.50 | 8.53 8.41 |
| 126 | [4-bromo-5-amino-2-ethoxycyclohexanoyl] | 1 | [3-chlorobenzyl] | Base | C₂₃H₂₇BrClN₃O₂ | 492.836 | 194 | 76 | Cal. Obt. | 56.05 56.06 | 5.52 5.60 | 8.53 8.52 |

TABLE I-continued
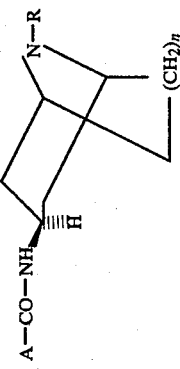
(I)
| Code n° | A—CO— | n | R | Form | Empirical formula | Molecular weight | Melting point (°C.) | Yield (%) | ELEMENTARY ANALYSIS % | | C | H | N |
|---|---|---|---|---|---|---|---|---|---|---|---|---|---|
| 127 | Cl, H2N, CO—, OCH3 | 1 | (3-F-phenyl) | Base | $C_{22}H_{25}ClFN_3O_2$ | 417.901 | 160 | 80 | Cal. Obt. | | 63.23 63.23 | 6.03 6.17 | 10.06 10.16 |
| 129 | CO—, OMe, MeO | 1 | (4-Br-phenyl) | Base | $C_{23}H_{27}BrN_2O_3$ | 459.371 | 146 | 73 | Cal. Obt. | | 60.13 60.35 | 5.92 5.88 | 6.10 6.02 |
| 131 | Br, H2N, CO—, OMe | 1 | (2-F-phenyl) | Base | $C_{22}H_{25}BrFN_3O_2$ | 462.353 | 209 | 32 | Cal. Obt. | | 57.15 57.46 | 5.45 5.56 | 9.09 9.00 |
| 132 | Br, H2N, CO—, OMe | 1 | (furan) | Base | $C_{20}H_{24}BrN_3O_3$ | 434.325 | 214 | 35 | Cal. Obt. | | 55.30 55.33 | 5.57 5.55 | 9.68 9.53 |

TABLE I-continued
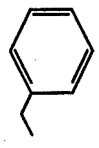
(I)
| Code n° | A—CO— | n | R | Form | Empirical formula | Molecular weight | Melting point (°C.) | Yield (%) | ELEMENTARY ANALYSIS % | | C | H | N |
|---|---|---|---|---|---|---|---|---|---|---|---|---|---|
| 135 | MeO—⟨⟩(OMe)(CO—)(MeO) | 1 | benzyl | Maleate | $C_{28}H_{34}N_2O_8$ | 526.568 | 160 | 75 | Cal. Obt. | | 63.86 63.78 | 6.51 6.71 | 5.32 5.06 |
| 139 | ⟨⟩(CO—)(OEt)(CH_3O) | 1 | benzyl | HCl | $C_{24}H_{31}ClN_2O_3$ | 430.961 | 245 | 78 | Cal. Obt. | | 66.88 66.99 | 7.25 7.13 | 6.50 6.54 |
| 140 | ⟨⟩(CO—)(OMe)(EtO) | 1 | " | HCl | $C_{24}H_{31}ClN_2O_3$ | 430.961 | 230 | 72 | Cal. Obt. | | 66.88 66.68 | 7.25 7.36 | 6.50 6.54 |
| 141 | MeO—⟨⟩(CO—)(OEt)(MeO) | 1 | " | HCl | $C_{25}H_{33}ClN_2O_4$ | 460.987 | 198 | 66 | Cal. Obt. | | 65.13 65.03 | 7.22 7.30 | 6.08 6.11 |

TABLE I-continued
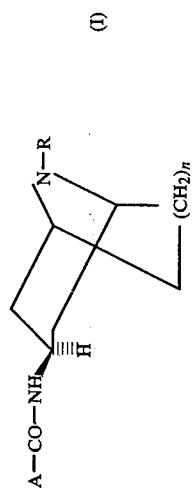
(I)
| Code n° | A—CO— | n | R | Form | Empirical formula | Molecular weight | Melting point (°C.) | Yield (%) | | ELEMENTARY ANALYSIS % | C | H | N |
|---|---|---|---|---|---|---|---|---|---|---|---|---|---|
| 142 | NO$_2$—⟨⟩—CO— with OMe, MeO | 1 | " | Base | C$_{23}$H$_{27}$N$_3$O$_5$ | 425.470 | 149 | 69 | Cal. Obt. | | 64.92 64.80 | 6.40 6.59 | 9.88 9.64 |
| 143 | ⟨⟩—CO— with OEt, MeO | 2 | " | HCl | C$_{25}$H$_{33}$ClN$_2$O$_3$ + 0.5% H$_2$O | 447.223 | 220 | 55 | Cal. Obt. | | 67.13 66.94 | 7.50 7.61 | 6.27 6.22 |
| 145 | ⟨⟩—CO— with OEt, MeO | 1 | 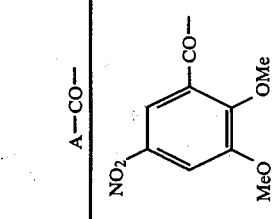 | HCl | C$_{24}$H$_{29}$Cl$_3$N$_2$O$_3$ | 499.859 | 240 | 79 | Cal. Obt. | | 57.66 57.81 | 5.85 6.03 | 5.60 5.87 |
| 147 | Br—⟨⟩—CO— with OMe, MeO | 1 | 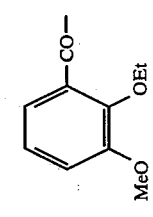 | Base | C$_{23}$H$_{27}$BrN$_2$O$_3$ | 459.371 | 154 | 54 | Cal. Obt. | | 60.13 60.43 | 5.92 5.78 | 6.10 6.15 |
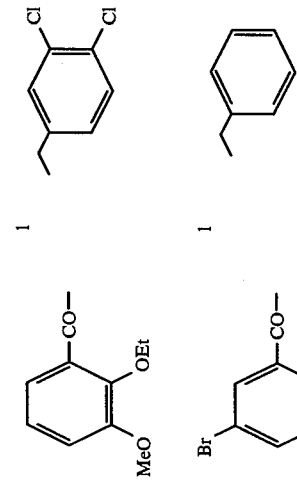

TABLE I-continued
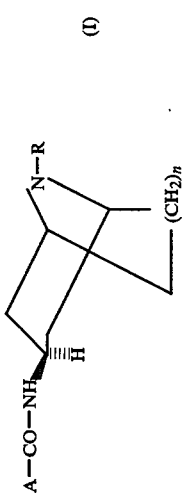
(I)
| Code n° | A—CO— | n | R | Form | Empirical formula | Molecular weight | Melting point (°C.) | Yield (%) | | % | ELEMENTARY ANALYSIS C | H | N |
|---|---|---|---|---|---|---|---|---|---|---|---|---|---|
| 148 | CO—, OMe, MeO | 2 | " | HCl | $C_{24}H_{31}ClN_2O_3$ | 430.961 | 217 | 70 | Cal. Obt. | | 66.88 66.58 | 7.25 7.32 | 6.50 6.47 |
| 155 | CO—, OMe, MeO | 1 | 4-F-C6H4 | HCl | $C_{23}H_{28}ClFN_2O$ | 434.927 | 226 | 80 | Cal. Obt. | | 63.51 63.61 | 6.49 6.61 | 6.44 6.68 |
| 168 | CO—, OMe, MeO, CH3S | 1 | C6H5 | Base | $C_{24}H_{30}N_2O_3S$ | 426.56 | 90 | 81 | Cal. Obt. | | 67.57 67.52 | 7.09 7.32 | 6.57 6.33 |
| 169 | CO—, OMe, Cl, H2N | 1 | 3-CH3-C6H4 | Base | $C_{23}H_{28}ClN_3O_2$ | 413.935 | 190 | 75 | Cal. Obt. | | 66.73 66.75 | 6.87 6.78 | 10.15 10.18 |

TABLE I-continued

![Structure (I): bicyclic amine with A—CO—NH on one side and N—R with (CH₂)ₙ bridge]

| Code n° | A—CO— | n | R | Form | Empirical formula | Molecular weight | Melting point (°C.) | Yield (%) | ELEMENTARY ANALYSIS % | | C | H | N |
|---|---|---|---|---|---|---|---|---|---|---|---|---|---|
| 171 | CH₃CO—, OMe, MeO (substituted benzoyl) | 1 | benzyl | Base | C₂₅H₃₀N₂O₄ | 422.51 | 131 | 53 | Cal. | | 71.06 | 7.16 | 6.63 |
| | | | | | | | | | Obt. | | 70.76 | 7.46 | 6.75 |
| 173 | OMe, MeO (substituted benzoyl) | 1 | 3-Cl-benzyl | Base | C₂₃H₂₇ClN₂O₃ | 414.92 | 91 | 76 | Cal. | | 66.57 | 6.56 | 6.75 |
| | | | | | | | | | Obt. | | 66.74 | 6.58 | 6.73 |
| 174 | EtS, OMe, MeO (substituted benzoyl) | 1 | benzyl | Oxalate | C₂₇H₃₄N₂O₇S | 530.62 | 167 | 71 | Cal. | | 61.11 | 6.46 | 5.28 |
| | | | | | | | | | Obt. | | 60.83 | 6.39 | 5.04 |
| 180 | OMe, MeO (substituted benzoyl) | 1 | 4-CN-benzyl | HCl + 1% H₂O | C₂₄H₂₈ClN₃O₃ + 1% H₂O | 446.41 | 260 | 78 | Cal. | | 64.57 | 6.44 | 9.41 |
| | | | | | | | | | Obt. | | 64.20 | 6.27 | 9.26 |

The compounds of formula (I) were tested on laboratory animals and showed an activity on the central nervous system (more especially a neuroleptic action) and/or on the digestive system (more especially as accelerators of gastro-intestinal motricity and as antiemetics).

Thus, the psychotropic properties were demonstrated on the one hand on mice, particularly by means of the test of the antagonism to apomorphinic straightenings, which test is carried out according to the method described by G. Gouret et Coll. in the J. Pharmacol. (Paris) 1973, 4, 341 and on the other hand on rat, particularly by means of the test of the antagonism to apomorphine induced stereotypies which test is carried out according to the method described by P. A. J. Janssen, C. I. C. Niemegeers and A. H. M. Jageneau in Arzneim-Forsch. (1960), 10, 1003.

Furthermore, the stair case test carried out on rat according to the method described by M. H. Thiebot, P. Soubrie, P. Simon and J. R. Boissier in Psychopharmacologia (Berl) (1973), 31, 77, has demonstrated the slight sedative effect of compounds (I) with regard to their psychotropic effect.

To illustrate the invention, some results obtained with the compounds of formula (I) using the above tests are given in the following tables II and III.

TABLE II

| Compound tested Code numbers | Antagonism to apomorphinic straightenings (mice) ED 50 (mg/kg/i.p.) |
|---|---|
| 106 | 0.053 |
| 112 | 0.029 |
| 113 | 0.016 |
| 115 | 0.038 |
| 118 | 0.016 |
| 120 | 0.032 |
| 121 | 0.024 |
| 123 | 0.041 |
| 126 | 0.054 |
| 127 | 0.007 |
| 129 | 0.008 |
| 131 | 0.013 |
| 132 | 0.12 |
| 135 | 0.010 |
| 139 | 0.010 |
| 140 | 0.019 |
| 141 | 0.035 |
| 142 | 0.012 |
| 143 | 0.025 |
| 145 | 0.3 |
| 147 | 0.042 |
| 148 | 0.008 |
| 155 | 0.005 |
| 168 | 0.28 |
| 169 | 0.034 |
| 171 | 0.029 |
| 173 | 0.013 |
| 174 | 0.034 |
| 180 | 0.010 |

TABLE III

| Compounds tested Code numbers | Antagonism to the apomorphine induced stereotypies (rat) ED50 (mg/kg/p.o.) | Stair case test (rat) ED50 (mg/kg/p.o.) |
|---|---|---|
| 106 | 1.6 | 8 |
| 115 | 0.22 | 1.3 |
| 123 | 0.2 | 1.7 |
| 139 | 0.06 | 0.3 |
| 143 | 0.26 | 1.6 |
| 169 | 0.46 | 3.5 |

The activity on the digestive system was demonstrated by the gastric evacuation test on rats, carried out according to the following method. The compounds of formula (I) were administered orally simultaneously with 20 steel balls to wakeful rats starved for 20 hours. The action on the gastric evacuation of the compounds of formula (I) was evaluated 90 minutes after administration, by the percentage of animals whose stomach does not contain any ball, the balls being counted by radiological examination.

To illustrate the invention, some results obtained with the compounds of formula (I) in the above test are given in the following table.

TABLE IV

| Compounds tested Code numbers | Gastric evacuation (rat) | |
|---|---|---|
| | Dose (mg/kg/po) | % animals whose stomach contains no ball after 90 minutes |
| 132 | 0.6 | 25 |
| | 1.3 | 50 |
| | 5 | 75 |
| | 10 | 100 |
| 147 | 0.3 | 25 |
| | 0.6 | 63 |
| | 10 | 90 |

The antiemetic activity is demonstrated on wakeful dogs, starved for 20 hours, by the percentage of animals completely protected for 30 minutes against vomiting induced by a subcutaneous injection of apomorphine chlorhydrate (0.1 mg/kg) by oral administration (one hour before the apomorphine) of the compounds of formula (I). To illustrate the invention, some results obtained with the compounds of formula (I) in the above test are given in table V below.

TABLE V

| Compounds tested Code numbers | Antiemetic activity (dogs) | |
|---|---|---|
| | Dose (mg/kg/po) | % inhibition of vomiting induced by apomorphine |
| 132 | 0.01 | 100 |
| 147 | 0.1 | 100 |

The acute toxicity of the compounds of the invention was also tested intraperitoneally on mice. Table VI below gives, by way of examples, some results obtained.

TABLE VI

| Compounds tested Code numbers | Toxicity (mice) LD 50 (mg/kg/i.p.) |
|---|---|
| 106 | 160 |
| 112 | 220 |
| 113 | 140 |
| 115 | 53 |
| 118 | 90 |
| 120 | 100 |
| 121 | 250 |
| 123 | >400 |
| 126 | >400 |
| 127 | 200 |
| 129 | 180 |
| 131 | 250 |
| 132 | 200 |
| 135 | 70 |
| 139 | 76 |
| 140 | 70 |
| 141 | 115 |
| 142 | 87.5 |
| 143 | 110 |
| 145 | >400 |
| 147 | 165 |
| 148 | 100 |
| 155 | 140 |
| 169 | 70 |

TABLE VI-continued

| Compounds tested Code numbers | Toxicity (mice) LD 50 (mg/kg/i.p.) |
|---|---|
| 171 | 115 |
| 173 | 160 |
| 174 | 95 |
| 180 | 275 |
| 168 | 120 |

The difference between toxic doses and active doses allows the therapeutical use of the compounds of formula (I) in the treatment of disturbances of the psychism and/or of the digestive system.

They will be preferably administered in the form of pharmaceutical compositions comprising one or more compounds of formula (I), if need be in association with a pharmaceutically acceptable vehicle.

For example, they will be administered orally in the form of tablets, pills or capsules containing 50 to 300 mg of active ingredient (3 to 8 per day), in the form of a solution containing 0.1 to 1% of active ingredient (10 to 60 drops, once to three times per day), parenterally in the form of injectable ampoules containing 5 to 100 mg of active ingredient (3 to 8 ampoules per day).

We claim:

1. A compound having the formula

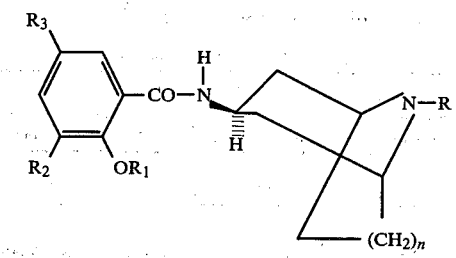

wherein n is 1; R is 3-furylmethyl, benzyl or benzyl in which the ring is substituted with one or two halogens, methyl or cyano; $R_1$ is methyl or ethyl; $R_2$ is methoxy or ethoxy; $R_3$ is hydrogen, bromine, methoxy, nitro, acetyl, methylmercapto or ethylmercapto, with the proviso that when the set ($R_3$, n, R) is (H, 1, benzyl) the set ($R_1$, $R_2$) is not ($CH_3$, $OCH_3$), and pharmacologically acceptable acid addition salts thereof.

2. A compound as claimed in claim 1 in which R is benzyl or benzyl in which the ring is substituted with one or two halogens, methyl or cyano, and $R_3$ is hydrogen, bromine, nitro or acetyl.

3. A compound as claimed in claim 1 in which n is 1; R is

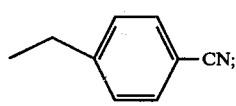

$R_1$ is methyl; $R_2$ is methoxy and $R_3$ is hydrogen.

4. A compound as claimed in claim 1 in which n is 1; R is

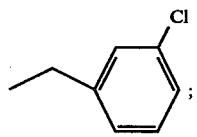

$R_1$ is methyl; $R_2$ is methoxy and $R_3$ is hydrogen.

5. A compound as claimed in claim 1 in which n is 1; R is

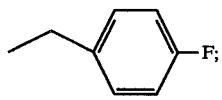

$R_1$ is methyl; $R_2$ is methoxy and $R_3$ is hydrogen.

6. A compound as claimed in claim 1 in which n is 1; R is

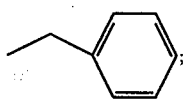

$R_1$ is methyl; $R_2$ is methoxy; and $R_3$ is bromine.

7. A compound as claimed in claim 1 in which n is 1; R is

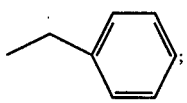

$R_1$ is ethyl; $R_2$ is methoxy; and $R_3$ is hydrogen.

8. A compound as claimed in claim 1 in which n is 1; R is

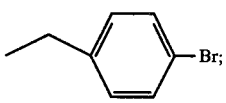

$R_1$ is methyl; $R_2$ is methoxy; and $R_3$ is hydrogen.

9. A compound as claimed in claim 1 in which n is 1; R is

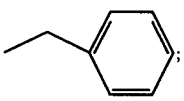

$R_1$ is ethyl; $R_2$ is ethoxy; and $R_3$ is hydrogen.

10. A compound as claimed in claim 1 in which n is 1; R is

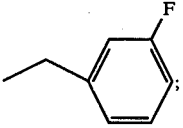

$R_1$ is methyl; $R_2$ is methoxy; and $R_3$ is hydrogen.

11. A compound as claimed in claim 1 in which n is 1; R is

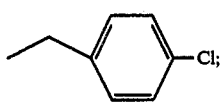

$R_1$ is methyl; $R_2$ is methoxy; and $R_3$ is hydrogen.

12. A compound having the formula

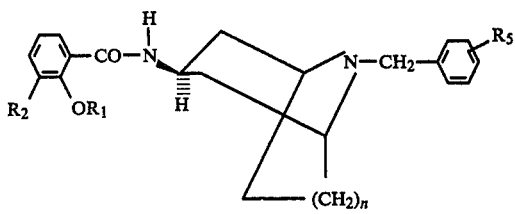

wherein n is 1; $R_5$ is halogen, methyl or cyano; $R_1$ is methyl or ethyl; $R_2$ is methoxy or ethoxy, and pharmacologically acceptable acid salts thereof.

13. A compound having the formula

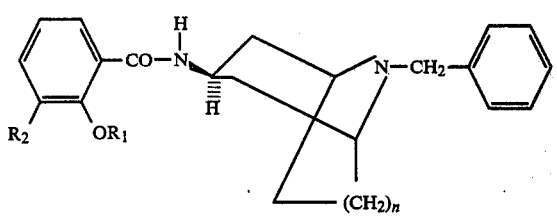

wherein n is 1; $R_1$ is methyl or ethyl; and $R_2$ is methoxy or ethoxy, with the proviso that the set $(R_1, R_2)$ is not $(CH_3, OCH_3)$, and pharmacologically acceptable acid addition salts thereof.

14. The compound as claimed in claim 1, in which the set of substituents (n, $R_1$, $R_2$, $R_3$, R) is selected from the group consisting of (1, Et, EtO, H, Benzyl), (1, $CH_3$, $OCH_3$, $OCH_3$, benzyl), (1, Et, $CH_3O$, H, Benzyl), (1, $CH_3$, EtO, H, benzyl), (1, Et, $CH_3O$, $CH_3O$, benzyl), (1, $CH_3$, $OCH_3$, $NO_2$, benzyl), (1, $CH_3$, $OCH_3$, Br, benzyl), (1, $CH_3$, $OCH_3$, $SCH_3$, benzyl), (1, $CH_3$, $OCH_3$, $SC_2H_5$, benzyl), (1, $CH_3$, $OCH_3$, $COCH_3$, benzyl),

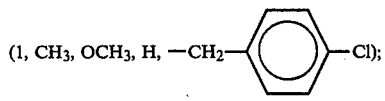

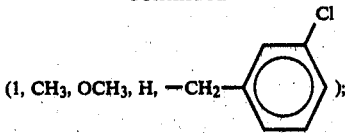

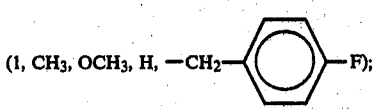

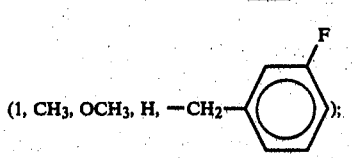

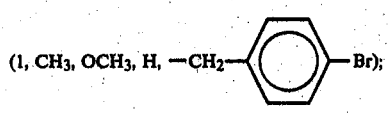

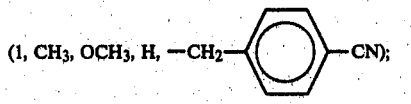

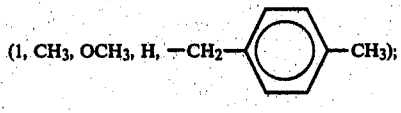

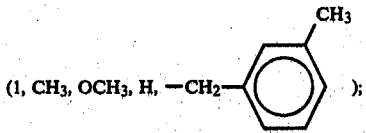

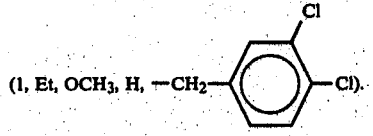

15. A psychotropic pharmaceutical composition comprising a therapeutically effective amount of a compound as claimed in claim 1, in combination with a pharmaceutically acceptable carrier.

16. An anti-emetic or anti-constipation pharmaceutical composition for treating the digestive system comprising a therapeutically effective amount of a compound as claimed in claim 1, in combination with a pharmaceutically acceptable carrier.

* * * * *

UNITED STATES PATENT AND TRADEMARK OFFICE
CERTIFICATE OF CORRECTION

PATENT NO. : 4,434,170

DATED : February 28, 1984

INVENTOR(S) : Philippe Dostert et al

It is certified that error appears in the above-identified patent and that said Letters Patent is hereby corrected as shown below:

Column 29, Line 22: after "acid" insert ---addition---.

Signed and Sealed this

Seventh Day of August 1984

[SEAL]

Attest:

GERALD J. MOSSINGHOFF

Attesting Officer

Commissioner of Patents and Trademarks